(12) United States Patent
Bernert et al.

(10) Patent No.: US 9,089,286 B2
(45) Date of Patent: Jul. 28, 2015

(54) OPTICAL SYSTEM FOR FOLLOWING OCULAR MOVEMENTS AND ASSOCIATED SUPPORT DEVICE

(75) Inventors: Frederic Bernert, Marseilles (FR); Mickael Maillard, Puteaux (FR); Serge Kinkingnehun, Vitry sur Seine (FR)

(73) Assignee: E(YE)BRAIN, Ivry sur Seine (FR)

( * ) Notice: Subject to any disclaimer, the term of this patent is extended or adjusted under 35 U.S.C. 154(b) by 125 days.

(21) Appl. No.: 13/639,121

(22) PCT Filed: Apr. 7, 2011

(86) PCT No.: PCT/FR2011/050782
§ 371 (c)(1),
(2), (4) Date: Oct. 3, 2012

(87) PCT Pub. No.: WO2011/124852
PCT Pub. Date: Oct. 13, 2011

(65) Prior Publication Data
US 2013/0027665 A1   Jan. 31, 2013

(30) Foreign Application Priority Data

Apr. 9, 2010  (FR) ...................................... 10 52720

(51) Int. Cl.
*A61B 3/14*   (2006.01)
*A61B 3/10*   (2006.01)
(Continued)

(52) U.S. Cl.
CPC ............... *A61B 3/113* (2013.01); *A61B 5/6803* (2013.01)

(58) Field of Classification Search
CPC ............ A61B 3/10; A61B 3/113; A61B 5/11; A61B 5/1114; A61B 2017/00216; A61B 5/0496; A61B 5/6803; A61M 2205/507; G02B 27/017

USPC ..................... 351/205, 208, 221, 209; 396/51
See application file for complete search history.

(56) References Cited

U.S. PATENT DOCUMENTS 4,102,564 A * 7/1978 Michael ......................... 351/210
4,712,895 A * 12/1987 Kamiyama et al. ........... 351/243
(Continued)

FOREIGN PATENT DOCUMENTS

| JP | 2009-240551 | 10/2009 |
| WO | 2008/141460 | 11/2008 |
| WO | 2009/043927 | 4/2009 |

OTHER PUBLICATIONS

International Search Report dated Aug. 5, 2011, corresponding to PCT/FR2011/050782.

*Primary Examiner* — Scott J Sugarman
*Assistant Examiner* — Collin X Beatty
(74) *Attorney, Agent, or Firm* — Young & Thompson (57) ABSTRACT

An optical system (100) for following ocular movements of an individual includes: an acquisition module (190) designed so as to acquire an image (Im) of the two eyes (22, 22*d*, 22*g*) of the individual, an optical element of transmission (110*d*, 110*g*), to the acquisition module, of two images (lm_d, lm_g) of respectively each eye which together correspond to a discontinuous region (24*d*, 24*g*) of the face, by multiple reflections along two optical routes (TOd, TOg) devoid of any semireflecting mirror. The optical routes further include optical input paths (114*d*, 114*g*) opposite respectively each eye, which are parallel to one another and to an optical axis (Z) of the acquisition module, and the optical element of transmission is configured so as to bring the two images closer together so that the acquisition module acquires the two images simultaneously.

20 Claims, 2 Drawing Sheets

(51) Int. Cl.
*A61B 3/113* (2006.01)
*A61B 5/00* (2006.01)

(56) References Cited

U.S. PATENT DOCUMENTS

| | | | |
|---|---|---|---|
| 4,838,678 A * | 6/1989 | Hubertus | 351/205 |
| 4,852,988 A * | 8/1989 | Velez et al. | 351/210 |
| 5,150,137 A | 9/1992 | Owens, II et al. | |
| 5,357,293 A * | 10/1994 | Uomori et al. | 351/209 |
| 5,530,495 A * | 6/1996 | Lamprecht | 351/210 |
| 5,714,967 A * | 2/1998 | Okamura et al. | 345/8 |
| 5,867,587 A * | 2/1999 | Aboutalib et al. | 382/117 |
| 5,963,300 A | 10/1999 | Horwitz | |
| 6,003,991 A | 12/1999 | Viirre | |
| 6,089,716 A * | 7/2000 | Lashkari et al. | 351/221 |
| 6,120,461 A | 9/2000 | Smyth | |
| 6,149,272 A * | 11/2000 | Bergner et al. | 351/221 |
| 6,231,187 B1 * | 5/2001 | Munoz et al. | 351/209 |
| 6,386,706 B1 * | 5/2002 | McClure et al. | 351/237 |
| 7,338,166 B2 * | 3/2008 | Waldorf et al. | 351/205 |
| 2003/0030899 A1 * | 2/2003 | Nakamura | 359/385 |
| 2005/0280603 A1 | 12/2005 | Aughey et al. | |
| 2006/0210111 A1 | 9/2006 | Cleveland et al. | |
| 2008/0192204 A1 * | 8/2008 | Prat Bartomeu | 351/209 |
| 2008/0278685 A1 * | 11/2008 | MacDougall et al. | 351/206 |
| 2008/0284979 A1 * | 11/2008 | Yee et al. | 351/209 |
| 2009/0213329 A1 * | 8/2009 | Kandel et al. | 351/206 |
| 2011/0077548 A1 * | 3/2011 | Torch | 600/558 |
| 2011/0085135 A1 * | 4/2011 | Bertolli | 351/206 |
| 2011/0170067 A1 * | 7/2011 | Sato et al. | 351/209 |
| 2012/0280893 A1 * | 11/2012 | Holakovszky | 345/8 |

* cited by examiner

OPTICAL SYSTEM FOR FOLLOWING OCULAR MOVEMENTS AND ASSOCIATED SUPPORT DEVICE

BACKGROUND OF THE INVENTION

The present invention relates to an optical system for tracking ocular movements of an individual and an associated support-type device worn on the head like a helmet.

DESCRIPTION OF THE RELATED ART

The tracking of ocular movements takes place in numerous applications, medical as well as technological or marketing.

For example, eye-movement analysis constitutes an aid to medical diagnosis, in particular in the diagnosis of neurological and psychiatric diseases such as neurodegenerative diseases including parkinsonian syndromes.

This analysis also makes it possible to deepen understanding in research fields such as visual exploration, visual strategy or the exploration of pathologies.

Another field of application is the detection of ocular movements in order to control electronic systems, such as for example the control of a computer pointer or of a high resolution display, by eye gaze.

Conventional optical systems for tracking ocular movements for medical purposes generally utilize the acquisition of an image of one or both eyes of a patient by means of one or more cameras, then analyze the image by a processing device in order to deduce the ocular movements therefrom.

These optical systems conventionally position a semi-reflective mirror between the eyes of the patient and an object that he is looking at. By reflection, this semi-reflective mirror returns part of the image of the eyes towards the camera or cameras arranged outside the patient's field of view. This is for example the case with the device described in the publication U.S. Pat. No. 5,150,137.

Certain optical systems use a camera for each eye. In this case, the presence of the two cameras makes these systems bulky and therefore difficult to utilize in a portable manner.

As for the optical systems which use the same camera for both eyes, these must be positioned at a distance from the eyes in order to be able to acquire an image including both of them. This distance presents a few drawbacks, and in particular a lower definition (in pixels) allocated to each eye in the image and the introduction of optical distortions. Analysis of the images in order to deduce ocular movements from them therefore proves more difficult.

In all of these optical systems, the presence of a semi-reflective mirror in the patient's field of view also constitutes a significant drawback, for at least two reasons. On the one hand, the semi-reflective mirror can constitute a reference zone for the patient, who can then use it as a reference point in exercises or tests performed, and therefore falsify the latter. On the other hand, the attenuation resulting from the separation of the light beams into two can result in it being more difficult for the patient to view the subject looked at and greater sensitivity being needed for the cameras.

Certain, more compact, devices have moreover been developed recently, allowing their portable use.

This is the case for example with the device for tracking ocular movements described in the publication US 2005/280603, relating in particular to an application of control of the display resolution, by zones, of a flight simulator.

The device described is in the form of a helmet provided to be placed on a user's head. The helmet comprises a semi-reflective visor mounted integral with the helmet and placed in the user's field of view, and a camera integral with the helmet and placed on the top part of the helmet outside the field of view.

The camera acquires an image of the eyes, and more precisely of the pupils, by simple reflection off the visor, the latter having in particular a concave internal surface making it possible to cause the reflected image of the area of the face comprising the eyes to converge towards the camera.

This device, although compact, has a certain number of drawbacks, and in particular those mentioned previously in connection with the use of a semi-reflective mirror.

Moreover, the concavity of the internal surface of the latter introduces significant optical distortions, and a loss of definition (in pixels) of the images of the eyes compared with the use of one camera for each eye. It is therefore necessary, in order to achieve accurate tracking of the ocular movements, to have recourse to suitable adaptive treatments, at the level of the processing device.

SUMMARY OF THE INVENTION

The present invention aims to overcome at least one of the drawbacks of the state of the art.

In this context, the invention relates in particular to an optical system for tracking the ocular movements of an individual's face, comprising an image-acquisition module arranged in order to acquire an image of both the individual's eyes, characterized in that it comprises an optical means of transmission, towards the acquisition module, of two images of each eye respectively which together correspond to a discontinuous region of the face by multiple reflections along two optical paths devoid of any semi-reflective mirror. In the optical system according to the invention, the optical paths comprise input optical paths in respect of each eye respectively, which are parallel to each other and to an optical axis of the image-acquisition module, and the optical means of transmission is configured in order to bring said two images closer together so that the acquisition module acquires said two images simultaneously.

Using a single acquisition module, the optical system according to the invention offers definitions (in pixels) substantially equivalent to systems using two cameras. By definition, the system is in particular positioned between the individual's eyes and the acquisition module.

This improved definition is obtained by the transmission of images corresponding to a discontinuous region of the face and by bringing these images closer together for their acquisition by the module dedicated to this purpose. Thus, the area of the face which is not transmitted, generally the area of discontinuity situated between the two eyes, is not acquired. The pixels conventionally used for the acquisition of this area between the two eyes are now allocated to the definition of the non-contiguous areas surrounding the eyes, by bringing the images closer together over a part of the discontinuity. The definition of these areas is improved as a result.

The bringing of the images closer together is in particular carried out along an axis parallel to that defined by both eyes, i.e. generally a horizontal axis.

The optical system according to the invention is moreover light as it comprises only one single acquisition module for both eyes.

The optical system according to the invention is also fairly compact as the optical means for bringing the images closer together makes it possible to avoid the significant distance conventionally necessary between the acquisition module and the eyes.

The optical system according to the invention can therefore be advantageously utilized in a portable fashion, for example on a helmet provided to be worn on the individual's head.

The images of both eyes acquired by the optical system according to the invention are conventionally transmitted to a processing device which, by analysis, will deduce from them the ocular movements of the individual.

The invention as defined here can be used in numerous fields as mentioned previously: medical, technological, marketing, etc.

In an embodiment of the invention, said optical means of transmission brings said two images closer together by multiple reflections using plane mirrors. This arrangement makes it possible to limit the optical distortions introduced by bringing the images closer together. In fact, the plane mirrors retain the dimensions of the reflected objects.

However, the invention is not limited to the use of plane mirrors, and non-plane mirrors can be utilized to the extent that their arrangement allows multiple reflections projecting the images of both eyes simultaneously onto the image-acquisition module.

In particular, the optical transmission means comprises two optical assemblies each provided with an input zone to be placed opposite each eye, and each optical assembly comprises a first mirror opposite the corresponding input zone and a second mirror opposite said first mirror and image-acquisition module. In this configuration, the optical system makes it possible to capture areas of high definition around each eye and optically bring them closer together so that they are acquired simultaneously by the same acquisition module.

Although the invention is not limited to this configuration, the latter has less complexity in order to ensure the effectiveness of the invention. In particular, the mirrors are configured in order to reflect the light rays, substantially at 90°. This angle is suited in particular to the case where the optical means of transmission is configured to bring the optical paths (at the level of the input zones) which are substantially parallel, closer together while retaining their parallelism when they are projected onto the acquisition module. The retention of this parallelism guarantees the absence of optical distortion on the acquired images of the eyes.

According to a particular feature, said second mirrors of the two optical assemblies are contiguous. This arrangement offers an optimization of the detection surface constituted by the acquisition module. In fact, the acquired image in this case comprises the two acquired non-contiguous portions of the face, in a contiguous manner. Thus no detection pixel is lost. This of course results in optimum definition of the acquired image portions for each eye.

In particular, the contiguous edge of said second mirrors is placed substantially in the optical axis of the image-acquisition module. In this way, the detection surface is equally divided for acquisition of the image portions for both eyes. Moreover, this configuration minimizes the optical distortions of the acquired images.

In an embodiment, the optical paths comprise output optical paths striking said image-acquisition module, which are parallel to each other and to the optical axis of the image-acquisition module.

In an embodiment, the optical system comprises, at the level of two input zones of the optical means of transmission to be placed opposite each eye, an optical wavelength filtering means. This makes it possible to filter the light signals entering the system at the level of the input zones, in particular in order to retain only the wavelengths effectively detected by the acquisition module. Any interference with the acquisition of the image of both eyes is thus avoided.

Similarly, the optical system comprises, at the level of two input zones of the optical means of transmission to be placed opposite each eye, a means of polarizing the light signals entering the system at the level of the input zones. This arrangement makes it possible to reduce the reflections present on the individual's eyes. This results in more effective detection and analysis of the ocular movements.

In an embodiment, the optical system is devoid of any semi-reflective mirror arranged in order to propagate an image of an eye towards the acquisition module and an image of an object towards the individual's eyes, the one by transmission through the semi-reflective mirror and the other by reflection off the semi-reflective mirror. In this case, no semi-reflective mirror is positioned on the optical path between the input zones and the image-acquisition module.

In the absence of a semi-reflective mirror, the system according to the invention has a reduced weight and is not placed directly in the individual's field of view. The optical system therefore has better visibility of the object viewed. As will be seen below, the optical system according to the invention can be placed just below the individual's main field of view.

According to a feature of the invention, the optical system comprises infrared illumination means, each for directly illuminating one of the two eyes, said illumination means operating with continuous emission. The fact that it is not necessary to use a semi-reflective mirror in the invention (which semi-reflective mirror introduces substantial attenuation of the luminosity received) and the proximity of the acquisition module to the eyes mean that the present invention makes it possible to effectively use infrared diodes of lower intensity. This results in the possibility of continuous emission and more long-term exposure of the user in order to follow his ocular movements without putting him at risk.

According to a feature of the invention, the optical system is mounted articulated on an attachment arm. This arrangement makes it possible, in particular when the individual adopts a predefined position relative to the attachment arm (for example a location provided for his head), to adjust the orientation of the optical system so that the two input zones are accurately positioned opposite both individual's eyes. This articulation is therefore in particular along a horizontal axis, parallel to the axis formed by the two eyes.

The invention also relates to a support device, for example of helmet type, provided in order to be placed on the head of an individual having two eyes looking at an object in a plane of view, comprising an optical system for tracking ocular movements as defined above, and in which a main optical axis of the optical system forms an angle with the plane of view. This angle ensures the offset of the optical system with respect to the individual's field of view. Thus, the greater this angle, the better the field of view for the individual. However, when this angle assumes values that are too great, the acquired image can be distorted to a greater or lesser extent.

Thus, according to a particular feature, the angle between the main optical axis and the plane of view is comprised between 20° and 45°, the optical system being placed below the plane of view. It is thus possible both to adjust the device to the morphology of the individual, and also to adjust the field of view left free for him. Given the dimension of the optical system, this range of values makes it possible to leave a field of view free downwards, with an angle substantially comprised between 15° and 40°. Preferably, the angle between the main optical axis and the plane of view is chosen so that the angle of the field of view downwards is approximately 20°, offering a good compromise between non-distorted acquisition of the eyes and width of the field of view.

In an embodiment, the optical system is mounted on an attachment arm articulated relative to a support structure, so as to vary the angle between the main optical axis and the plane of view. An adjustment of the helmet to the morphology of the individual is therefore possible. This adjustment combined in particular with the rotational adjustment of the optical system with respect to the attachment arm (as mentioned previously) makes it possible to achieve an effective alignment of the input zones of the optical system with the user's eyes, irrespective of the morphology of the individual.

BRIEF DESCRIPTION OF THE DRAWING FIGURES

Other features and advantages of the invention will also become apparent from the description below, illustrated by the attached drawings, in which.

DETAILED DESCRIPTION OF THE INVENTION

Figure 1:
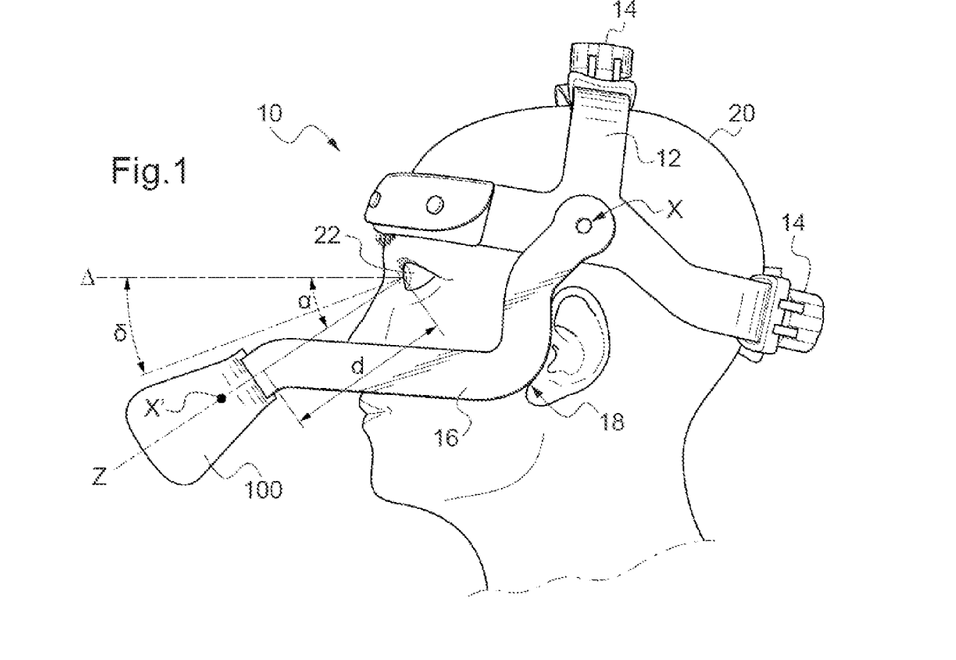
FIG. 1 represents a helmet-type device carrying an optical system according to the invention.

With reference to FIG. 1, a helmet-type support 10 for tracking the ocular movements of an individual comprises a helmet structure 12 provided in order to be adjusted to the head of an individual 20, for example using elastic means (holding elastic strap passing around the head) or mechanical adjustment means 14.

The helmet 10 also comprises two attachment arms 16 on either side of the individual's face, mounted mobile in rotation about the horizontal axis X relative to the structure 12.

The attachment arms 16 are bent and extend diagonally from the points of rotation situated at the height of the individual's temporal areas towards the lower part of the face, firstly by a substantially vertical section, then by a horizontal section. The bend 18 makes it possible, as the figure shows, to free the individual's side field of view.

At the end of the two attachment arms there is arranged, in an articulated manner about the horizontal axis X', an optical system 100 for tracking the ocular movements according to the invention. The optical system 100 has a main optical axis Z which, when the system is in use, is substantially aligned with the individual's eyes 22.

The optical system 100 can turn about the axis X' over an angular amplitude of approximately 10°, relative to an initial position for aligning the optical axis Z of the system 100 with the individual's eyes. This alignment in particular makes it possible to correctly centre the image of the eyes on an acquisition module of the images provided in the optical system.

As for the attachment arms 16, they can turn about the axis X between a position where the main optical axis Z of the system 100 forms an angle α with a plane of view Δ (here horizontal—plane formed by the eyes and an object viewed) of the individual equal to 20° and a position where this angle is 35°. In the example of the figure, the values of this angle are to be understood with the optical system 100 situated below the plane of view Δ. This freedom of rotation allows a vertical adjustment of the optical system 100 relative to the individual.

This range of values [20°, 45°] makes it possible in particular to position the optical system 100 so that the individual's field of view downwards (angle δ defined between the plane of view Δ and the top of the system 100) has an angle δ comprised between 15° and 40°. This angle of course depends on the dimensions of the optical system 100.

In particular, an angle α will be chosen such that the angle δ is comprised between 18° and 30°, and in particular equal to 20°, optimizing the ratio between the angular aperture of the field of view downwards and the distortion of the images of the eyes.

As illustrated in the figure, the length of the attachment arms 16 is provided so that the front surface (closest to the individual) of the optical system for tracking ocular movements is arranged at a distance d from the eyes, comprised between 7 and 10 cm, and in particular equal to 8 cm.

The optical system 100 for tracking the ocular movements has the function of acquiring a sequence of images of both the individual's eyes in order for an analysis to be carried out to determine the behaviour of the eyes (ocular movements).

All or part of the processing device (not shown) for carrying out this analysis can be carried in the optical system 100. Preferably however, in order to limit the complexity of the optical system 100, this processing device is mostly outside the helmet 10.

For example, only processing relating to the detection of the pupil and/or time-stamping of the image data can be carried out inside the helmet. In the first case, less information (than whole images) is transmitted to the external processing device. In the second case, this makes it possible to ensure the synchronization between the acquired images and visual stimuli presented to the individual, in order to correct any time delays or asynchronisms between the system 100 and the processing device.

Thus, the data collected by the optical system 100 and transmitted to the external processing device can be of different kinds, and in particular images or data relating to the position of each eye or data relating to speed, etc.

When the processing device is mostly outside the helmet, means of transmission, either by wires via a connector provided for this purpose at the level of the optical system 100 (192 in FIG. 2), or by waves (for example wifi, bluetooth or equivalent), are provided in order to transmit the image data. The optical system 100 is thus connected to the processing device for tracking ocular movements, which receives this image data. As such means of transmission, as well as the processing device, are widely known to a person skilled in the art, they will not be described in more detail here and can be in the form of one or more microcontrollers or processors.

It should however be noted that as the acquisition carried out here is in the form of images, the processing carried out in order to determine the individual's ocular behaviour are for example the analyses of images by detection of the eyes (or pupils) and by tracking the shapes detected from image to image.

Although FIG. 1 presents the invention in a portable-helmet context, the optical system 100 can be mounted mobile using an arm 16 for attaching to a fixed device on which the face of the individual to be analyzed is presented.

Figure 2:
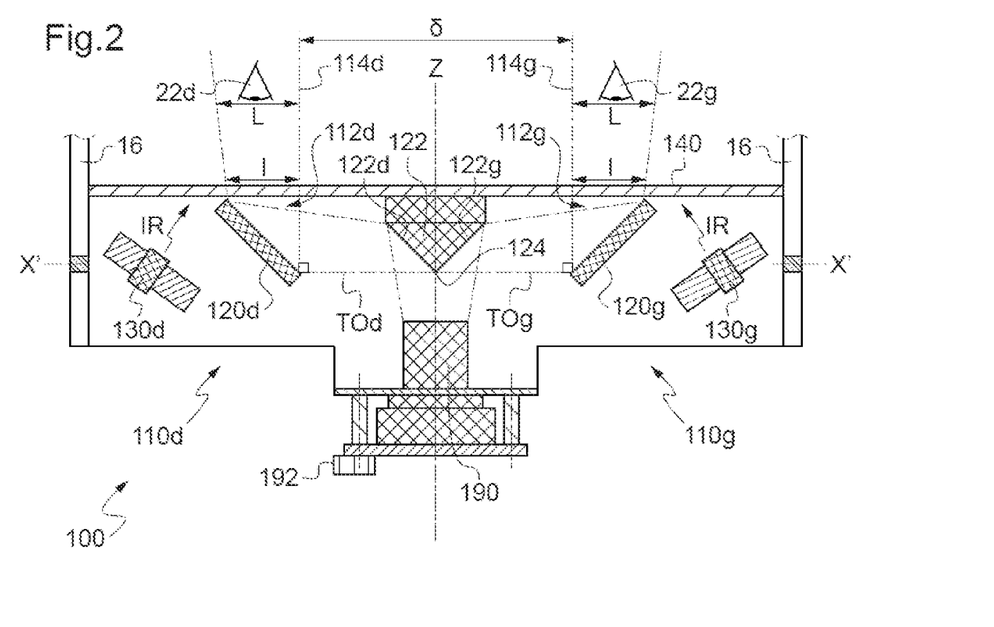
FIG. 2 represents a top view of an embodiment of an optical system according to the invention.

FIG. 2 illustrates in detail a top view of an embodiment of an optical system 100 according to the invention.

The optical system 100 comprises two optical assemblies 110*d* and 110*g* respectively associated with the individual's eyes, and arranged on the same support (not shown) of the system 100.

The right eye 22*d* is presented opposite the input zone 112*d* of the first optical assembly 110*d*, whereas the left eye 22*g* is presented opposite the input zone 112*g* of the second optical assembly 110*g*. The positioning of the input zones opposite the eyes is adjusted in particular via rotation of the optical system 100 about the axis X'.

The two optical assemblies 110*d* and 110*g* cooperate together in order to transmit the images of the eyes obtained at the input zones 112*d* and 112*g* towards an acquisition module 190 and in order to bring them closer together when they leave these optical assemblies again, so that they are acquired simultaneously by the camera-type acquisition module 190, such as CCD ("Charge-Coupled Device") and CMOS ("Complementary metal oxide semi-conductor") sensors well known to a person skilled in the art. The simultaneity here is due to the fact that the images of each eye reach the sensor together (spatially juxtaposed). Therefore the acquisition of an image by this sensor at a point in time t comprises the acquisition of the images of each eye.

As will be seen below with reference to FIG. 5, the two input zones are opposite two non-contiguous areas of the face. Thus, the two images transmitted, each by one of the optical assemblies, correspond to a discontinuous region of the individual's face.

In order to carry out a very accurate analysis of the tracking of the ocular movements the acquisition of images at high frequency, for example at 100 Hz or more and in particular at least 300 Hz will in particular be preferred.

The input zones 112*d* and 112*g* are not necessarily in the form of openings (generally round) made in a housing of the optical system 100 and therefore define particular zones of the system taking into account the optical paths described hereafter.

Figure 3:
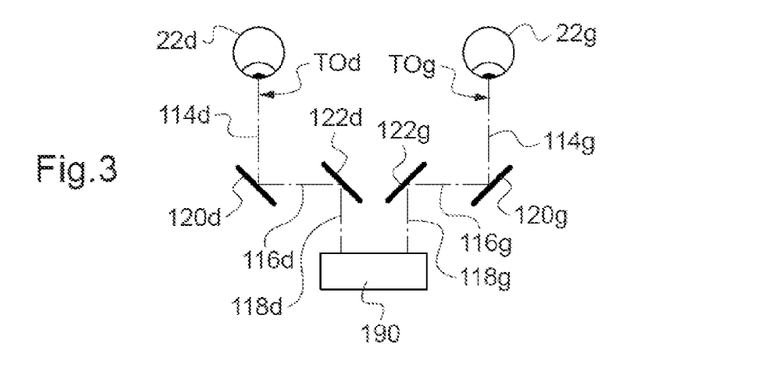
FIG. 3 illustrates diagrammatically the principle of bringing images optically closer together according to the invention.

As illustrated diagrammatically in FIG. 3, the principle of bringing the images closer together in this embodiment utilizes multiple reflections, in particular two reflections on plane mirrors.

The acquired image of each eye 22*d* or 22*g* travels an optical path TOd or TOg which is made up of an input optical path 114*d* or 114*g*, an intermediate optical path 116*d* or 116*g* and an output optical path 118*d* or 118*g*.

The input optical paths 114*d* and 114*g* are defined between the eyes 22*d* and 22*g* and a first plane mirror 120*d* or 120*g* in each assembly 110*d* and 110*g*. The input optical paths are preferably parallel to each other, and moreover parallel to the optical axis Z of the optical system 100.

The intermediate optical paths 116*d* and 116*g* run from each first plane mirror 120*d* or 120*g* to a second plane mirror 122*d* or 122*g*, according to the principles of optical reflection.

Finally, the output optical paths 118*d* and 118*g* run from the second mirrors 122*d* and 122*g* and the camera 190.

The arrangement of the mirrors shown here is such that the output optical paths are also parallel to each other and parallel to the optical axis Z. This results from the use of mirrors positioned at 45° relative to each optical path, so that the light rays along these optical paths are reflected at 90°.

The invention applies, however, to other positions of the mirrors, provided that the multiple reflections project the images of both eyes simultaneously onto the camera 190. Moreover, the aperture angle of the camera can cause these optical paths to vary slightly.

A camera with a short focal length, for example 8 mm, can be used to provide significant compactness. In this case, when the optical system is designed, a fine adjustment is made to the focussing of the camera 190, in order to take into account errors in the positioning of the mirrors in the optical system. It should be noted that the variations due to the variable shapes of individuals' faces can result in slight blurring in the acquisition of the images of the eyes, without however impairing the effectiveness of the algorithms for the detection of pupils and/or for tracking ocular movements.

As shown in FIG. 2, during operation, the first plane mirrors 120*d* or 120*g* are situated opposite the two eyes 22*d* and 22*g*. The input zones are therefore the zones in front of these first mirrors.

The first mirrors can in particular be formed by a gold-based reflective coating in order to obtain properties of maximum reflectivities in the visible spectrum close to the infrared and in the infrared, in particular a reflectivity coefficient of the order of 96% in the 750-1500 nm zone. However, other less effective coatings (aluminium- or silver-type metallic coating) can be used, the optical system 100 then being less luminous.

As these mirrors are not in the main zone (zone of interest) of vision of the individual 20, they do not need to be semi-reflective (i.e. still allowing part of the light radiation to pass through). As a result, mirrors which are not semi-reflective are used, i.e. mirrors in the accepted meaning of the word. Hereafter, unless specified as "semi-reflective" the mirror in question is a mirror in the accepted sense, with a property of total (or virtually total) reflection.

The image of each eye 22 is, in the example, reflected substantially at 90° by the first mirror 120 in order to be projected onto the second plane mirror 122 which is typically a triangular mirror two contiguous adjacent surfaces 122*d* and 122*g* of which, positioned at a right angle, constitute the two second mirrors of the optical assemblies 110*d* and 110*g*. Preferably, these mirrors also have a gold-based reflective coating.

Such a triangular mirror makes it possible to render the two images of both eyes contiguous after their reflection off this mirror. As is apparent from the figure, the bringing of the images of each eye closer together is a function of the movement of the two mirrors 122*d* and 122*g* away from each other or the movement away from the "useful" zone of these mirrors used for the reflection of the images of each eye. Thus, according to the desired embodiment, the two mirrors can be moved slightly apart so as not to bring the images completely together, or the "useful" zones can be shifted with respect to the contiguous edge 124, for example by shifting (along the axis Z towards the eyes) the first mirror 120 with respect to the second mirror 122.

In particular, the contiguous side 124 of the triangular mirror is placed in the optical axis (merged with the axis Z) of the camera 190. Thus, the two contiguous images of the eyes are detected equally (each one-half of the area of detection) by the camera.

Thus configured, the triangular mirror 122 makes it possible to send the image of each of the eyes back to half of the sensor of the camera.

The optical paths close to this axis Z follow, in the example of FIG. 2, reflections at a right angle so that the corresponding optical paths 114*d*/114*g* are parallel. The gap δ between these parallel optical paths corresponds to the width of the area of discontinuity between the eyes which is not acquired by the camera. Of course, if the two second mirrors 122 are not contiguous, this parallelism is retained only if the camera 190 has a wide aperture angle. In this case the gap δ is clearly increased.

It will be noted here that no semi-reflective mirror is necessary in the present invention in order to track the ocular movements, unlike the known devices.

In the diagram of FIG. 2, the projected length ";" of these mirrors on the glass pane 140 protecting the optical system is a few centimeters, for example between 1.4 and 2 cm.

By using a camera 190 having an appropriate aperture angle, this projected length "l" substantially delimiting what the camera 190 will acquire, corresponds to an area of the face around each eye which has a width "L" of the order of 5 to 7 cm (given the distance "d" of approximately 8 cm to the face). Thus, the optical system 100 according to the invention is tolerant to a variation in the distance between the eyes from one individual to another.

It should be noted that this aperture angle makes it possible to use second mirrors 122 with smaller dimensions than the first mirrors 120.

Geometrical relationships which are standard for the person skilled in the art connect all or some of the dimensions of the mirrors, the focal length and aperture angle of the camera, the distance "d", widths "l" and "L" and/or the distances separating the mirrors from each other or from the camera. Thus simple calculations make it possible, according to requirements, to determine one or other of these parameters (and therefore optionally choose suitable equipment) as a function of the others.

Figure 4:
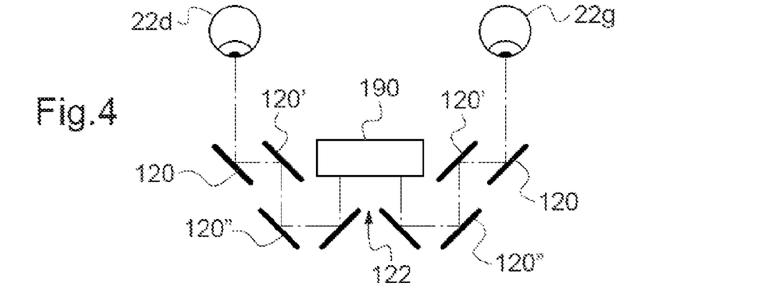
FIG. 4 illustrates an alternative to the diagram of FIG. 3.

Although the figure shows a camera arranged on the side opposite the optical system 100 with respect to the eyes 22, it can be provided on the same side as the eyes by reversing the direction of the triangular mirror (FIG. 4) where additional mirrors 120' and 120" are provided in order to add multiple reflections.

Returning to FIG. 2, an infrared radiation diode 130d or 130g is provided in each optical assembly 110 in order to directly illuminate the corresponding eye. In a manner well known per se, this infrared illumination makes it possible to improve the detection of the eyes in the images acquired by the camera 190, thanks to an enhancement of the contrast of the eye. Of course, this camera is by nature chosen as detecting in the wavelengths of the visible spectrum but also in the infrared corresponding to said diodes (generally an infrared close to the visible, for example an 830 nm diode).

Due mainly to the absence of a semi-reflective mirror attenuating the acquired images, but also due to the short distance between the optical system 100 and the eyes 22, the infrared illumination by the diodes 130 can be of low intensity and continuous compared to the known devices (illumination of higher intensity and pulsed due to risks linked to the exposure of the eyes to the illumination). The device according to the invention can therefore advantageously be used continuously for a longer time on an individual, without presenting a risk to the eyes.

Optionally, the optical system 100 is equipped with a glass pane 140 at the level of the input zones 112, between the individual's eyes and the first mirrors 120. As a variant, two glass panes can be used, each placed at the level of one of the input zones.

The use of a glass pane 140, filtering or not, makes it possible to physically protect the optical system 100 (from dust entering for example).

Moreover, it is possible to choose a glass pane 140 which filters part of the visible spectrum whilst only slightly attenuating the light in the spectral band emitted by the diodes. The filtering glass pane 140 is then in particular chosen in order to allow the frequencies best detected by the camera 190 and/or the frequencies corresponding to the colours on the basis of which the subsequent processing, (detection of contours, pupils, etc.) is facilitated, to pass, in particular the visible spectrum close to the infrared and the infrared from.

By way of example, it is then possible to apply to the images obtained at the camera 190, a pupil detection algorithm by thresholding of the black if the contrast is sufficient and/or a pupil segmentation algorithm and/or an algorithm based on a search for models of pupils.

As a variant or in combination, the glass pane 140 can also be chosen polarizing, in order to eliminate or attenuate the reflections off the cornea of the eyes 22.

However, distinct filtering and polarization means can be provided, for example using two superimposed glass panes.

As is apparent from the description of this embodiment, the invention makes it possible in particular to use a single camera filming each of the eyes independently. The camera is placed close to the eyes, which makes it possible to avoid substantial optical distortions of the image of the eyes on the sensor of the camera and makes it possible to improve the definition in pixels of the image acquired for each eye.

Figure 5:
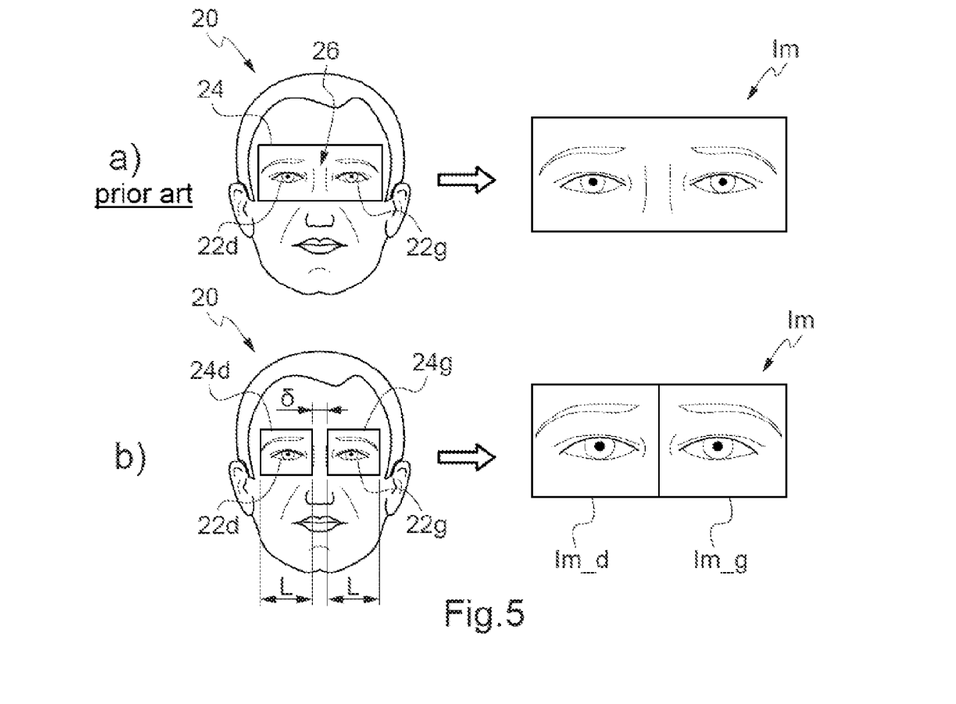
FIG. 5 illustrates the implementation of the invention for the acquisition of an image of the eyes of an individual, in comparison with the solutions of the state of the art.

FIG. 5 illustrates the bringing of the independent images of each eye closer together, in comparison with the known prior art (FIG. 5a).

In the prior art, the use of a single camera means that a single continuous area 24 of the face of the individual 20 is acquired in image 'lm'. This continuous area 24 comprises the areas relating to both eyes 22d and 22g but also the area 26 of the face situated between the individual's two eyes.

With the invention (FIG. 5b), two areas 24d and 24g of the face which are independent, non-contiguous and each centred on one of the two eyes, are acquired by the camera 190. As shown in the figure, these two areas correspond to a discontinuous region of the individual's face and the system 100 projects this discontinuous region in a continuous image onto the sensor of the camera 190. Thus, the optical system 100 according to the invention avoids the acquisition of the area 26 between the two eyes as it is not reflected by the first mirrors 120d and 120g.

As a variant, part of the area 26 can be reflected by the first mirrors, but not transmitted as far as the acquisition module due, for example, to the absence of reflection by the second mirrors 122d and 122g. In order to achieve this absence of reflection, these second mirrors can be of reduced dimensions and arranged so as to reflect only a sub-section of what has been reflected by the first mirrors. This sub-section is then the area 24d or 24g, depending on the optical assembly considered. In this case, the non-transmission of the area 26 results from the absence of reflection partly by the first mirrors and partly by the second mirrors.

The optical system 100 according to the invention therefore makes it possible to optically bring the images (lm_d and lm_g) relating to the two areas 24d and 24g closer together so that they can be detected close together by the camera. This bringing closer together is carried out on all or part of the discontinuity between the two areas, i.e. on all or part of the area 26 between the two eyes. Thus, "close together" means that the distance between the two eyes on the sensor of the camera is less than the distance between the two eyes on the face after transformation by the optical system (in fact the optical system can insert a slight modification of the distances, even if the use of plane mirrors makes it possible to limit the latter). In other words, the two eyes in the image obtained by the invention have been brought closer together than if they had been obtained by the same system acquiring the entire area of the face including the area 26 between the eyes.

In particular, as shown in the figure, the two detected images lm_d and lm_g are contiguous, thanks in particular to the use of contiguous mirrors 122*d* and 122*g* (triangular mirror).

This optical bringing closer together makes it possible to reduce the optical distance between the camera 190 and the eyes 22 relative to the long distances required in a number of systems of the state of the art, so that the image 'lm' of the eyes has a better definition for each eye. In fact, the pixels conventionally used for the acquisition of the area 26 between the two eyes are now allocated to the acquisition of images lm_d and lm_g of the areas 24*d* and 24*g* centred on the eyes.

The above examples are only embodiments of the invention which is not limited to them.

In particular, although an optical system 100 is described arranged below the direction of vision of the individual, the optical system 100 according to the invention can be positioned above this direction (obtaining a 15° to 40° viewing angle upwards depending on the rotation of the arms 16), but also on one side of the individual's field of view, making it possible, depending on the constraints imposed, to release a maximum field of view under preferred directions.

The invention claimed is:

1. Optical system for tracking the ocular movements of an individual's face, comprising:
    an image acquisition module arranged in order to acquire an image of both the eyes of the individual,
    an optical means of transmission, towards the acquisition module, of two images of each eye respectively, which together correspond to a discontinuous region of the face by multiple reflections along two optical paths devoid of any semi-reflective mirror,
    wherein the two optical paths comprise input optical paths in respect of each eye respectively, which are parallel to each other and to an optical axis of the image-acquisition module,
    wherein the optical means of transmission is configured in order to bring said two images closer together so that the acquisition module acquires said two images simultaneously, and
    wherein said optical means of transmission brings said two images closer together by multiple reflections using plane mirrors,
    infrared illumination means that directly illuminate one of the two eyes with infrared light, said illumination means operating with continuous emission, and
    a combination of i) a filter that filters part of a visible spectrum while allowing the infrared light to pass, and ii) a polarizer of the light signals entering the system at the input zones at the level of two input zones of the optical means of transmission to be placed opposite each eye,
    wherein the infrared light emitted by the infrared illumination means passes through the polarizer and the filter to illuminate the eyes and infrared light reflected by the eyes also passes through the polarizer and filter when entering the system at the input zones.

2. Optical system according to claim 1, wherein the optical means of transmission comprises two optical assemblies each provided with an input zone to be placed opposite each eye, and each optical assembly comprises only two mirrors between the corresponding input zone and the image-acquisition module, the two mirrors including a first mirror opposite the corresponding input zone and a second mirror opposite said first mirrors and image-acquisition module.

3. Optical system according to claim 2, in which said second mirrors of the two optical assemblies are contiguous to render the two images contiguous to the image-acquisition module.

4. Optical system according to claim 3, in which the contiguous edge of said second mirrors is placed substantially in the optical axis of the image-acquisition module.

5. Optical system according to claim 1, in which the optical paths comprise output optical paths striking said image-acquisition module, which are parallel to each other and to the optical axis of the image-acquisition module.

6. Optical system according to claim 1, in which the optical system is mounted articulated on an attachment arm.

7. Support device provided to be placed on the head of an individual having two eyes looking at an object in a plane of view, comprising an optical system for tracking ocular movements according to claim 1, and in which a main optical axis of the optical system forms a angle with the plane of view.

8. Device according to claim 7, in which the angle between the main optical axis and the plane of view is comprised between 20° and 45°, the optical system being placed below the plane of view.

9. Device according to claim 7, in which the optical system is mounted on an attachment arm articulated relative to a structure support, so as to vary the angle between the main optical axis and the plane of view.

10. Device according to claim 8, in which the optical system is mounted on an attachment arm articulated relative to a structure support, so as to vary the angle between the main optical axis and the plane of view.

11. Optical system according to claim 1, wherein the polarizer and the filter are formed of a same glass pane.

12. Optical system according to claim 1, wherein the polarizer and the filter are formed of two superimposed glass panes.

13. Optical system according to claim 1, wherein the optical means of transmission is further configured to time-stamp said two images, said two images with the time-stamps for transmission to and processing by a processing device, the time-stamps of said two images allowing synchronization between said two images and visual stimuli presented to the individual in order to correct any time delays or asynchronisms between the optical system and the processing device.

14. Optical system according to claim 1, wherein,
    the image acquisition module has a back side and an opposite forward side containing an optical entry, and
    the image acquisition module is arranged between the eyes and the plane mirrors of the optical system, with the back side of the image acquisition module facing the eyes of the individual and the front side containing the optical entry facing away from the eyes of the individual.

15. Optical system for tracking the ocular movements of an individual's face, comprising:
    an image acquisition module arranged to acquire an image of both the eyes of the individual;
    an optical means of transmission, towards the acquisition module, of two images of each eye respectively, which together correspond to a discontinuous region of the face by multiple reflections along two optical paths devoid of any semi-reflective mirror;
    wherein the two optical paths comprise input optical paths in respect of each eye respectively, which are parallel to each other and to an optical axis of the image-acquisition module,
    wherein the optical means of transmission is configured in order to bring said two images closer together so that the acquisition module acquires said two images simultaneously and time-stamps said two images, said two images with the time-stamps for transmission to and processing by a processing device, and wherein said optical means of transmission brings said two images closer together by multiple reflections using plane mirrors; and wherein the time-stamps of said two images allows synchronization between said two images and visual stimuli presented to the individual in order to correct any time delays or asynchronisms between the optical system and the processing device.

16. Support device provided to be placed on the head of an individual having two eyes looking at an object in a plane of view, comprising an optical system for tracking ocular movements according to claim 15, and in which a main optical axis of the optical system forms a angle with the plane of view.

17. Optical system according to claim 15, wherein, the image acquisition module has a back side and an opposite forward side containing an optical entry, and the image acquisition module is arranged between the eyes and the plane mirrors of the optical system, with the back side of the image acquisition module facing the eyes of the individual and the front side containing the optical entry facing away from the eyes of the individual.

18. Optical system according to claim 15, wherein the optical means of transmission comprises two optical assemblies each provided with an input zone to be placed opposite each eye, and each optical assembly comprises only two mirrors between the corresponding input zone and the image-acquisition module, the two mirrors including a first mirror opposite the corresponding input zone and a second mirror opposite said first mirrors and image-acquisition module.

19. Optical system according to claim 18, in which said second mirrors of the two optical assemblies are contiguous to render the two images contiguous to the image-acquisition module.

20. Optical system according to claim 19, in which the contiguous edge of said second mirrors is placed substantially in the optical axis of the image-acquisition module.

* * * * *